United States Patent
Gracey et al.

(10) Patent No.: US 8,367,886 B2
(45) Date of Patent: *Feb. 5, 2013

(54) REACTIVE DISTILLATION FOR THE DEHYDRATION OF MIXED ALCOHOLS

(75) Inventors: Benjamin Patrick Gracey, Hull (GB); Leslie William Bolton, Fleet (GB)

(73) Assignee: BP Chemicals Limited, Middlesex (GB)

( * ) Notice: Subject to any disclaimer, the term of this patent is extended or adjusted under 35 U.S.C. 154(b) by 775 days.

This patent is subject to a terminal disclaimer.

(21) Appl. No.: 11/988,226

(22) PCT Filed: Jun. 29, 2006

(86) PCT No.: PCT/GB2006/002419
§ 371 (c)(1),
(2), (4) Date: Jan. 3, 2008

(87) PCT Pub. No.: WO2007/003899
PCT Pub. Date: Jan. 11, 2007

(65) Prior Publication Data
US 2008/0275283 A1 Nov. 6, 2008

(30) Foreign Application Priority Data
Jul. 6, 2005 (EP) .................................... 05254235

(51) Int. Cl.
*C07C 1/20* (2006.01)
(52) U.S. Cl. ........ 585/639; 585/310; 585/315; 585/324; 585/640; 585/649; 585/651; 568/840; 260/449 R
(58) Field of Classification Search ........... 585/310, 585/315, 324, 639, 640, 649, 651; 568/840; 260/449 R
See application file for complete search history.

(56) References Cited

U.S. PATENT DOCUMENTS
3,974,232 A * 8/1976 Aizawa et al. ................ 585/357
(Continued)

FOREIGN PATENT DOCUMENTS
JP 55-19247 2/1980
WO WO 97/03932 A1 2/1997
(Continued)

OTHER PUBLICATIONS
International Search Report for PCT/GB2006/002419 mailed Oct. 17, 2006.
(Continued)

*Primary Examiner* — Prem C Singh
(74) *Attorney, Agent, or Firm* — Nixon & Vanderhye

(57) ABSTRACT

Process for producing alkene(s) from a feedstock containing at least one monohydric aliphatic paraffinic alcohol having from 2 to 5 carbon atoms. The process is carried out by 1 converting the monohydric aliphatic paraffinic alcohol(s) containing 2 to 5 carbon atoms in a reactive distillation column at elevated pressure and temperature into a heads stream having the corresponding same carbon number alkene(s) and ether(s), 2 separating the heads stream from step 1 into an ether(s) enriched stream and an alkene(s) enriched stream, 3 recycling at least part of the ether(s) enriched stream from step 2 as a reflux return to the reactive distillation column, 4 simultaneously separating the alkene(s) enriched stream from step 2 into alkene(s) and ether(s), and 5 recycling at least part of the separated ether(s) from step 4 into the reactive distillation column. An alkene(s) stream from step 4 is then recovered.

28 Claims, 1 Drawing Sheet

U.S. PATENT DOCUMENTS

| | | | |
|---|---|---|---|
| 4,014,913 A * | 3/1977 | Ellgen et al. | 518/716 |
| 4,396,789 A | 8/1983 | Barrocas et al. | |
| 4,398,050 A | 8/1983 | Hofstadt et al. | |
| 4,698,452 A * | 10/1987 | Le Van Mao et al. | 585/640 |
| 5,811,620 A | 9/1998 | Knifton et al. | |
| 5,817,906 A * | 10/1998 | Marker et al. | 585/640 |
| 5,849,971 A | 12/1998 | Sakuth et al. | |

FOREIGN PATENT DOCUMENTS

| | | |
|---|---|---|
| WO | 2001/44145 | 6/2001 |

OTHER PUBLICATIONS

Database WPI, Section Ch, Week 198012, *Derwent Publications Ltd.*, AN 1980-21248C XP002361053.

Russian Office Action dated Mar. 6, 2010; issued in corresponding Russian Patent Application No. 2008 103 615 (3 pgs); English Translation of Russian Office Action dated Apr. 22, 2010 (3 pgs).

* cited by examiner

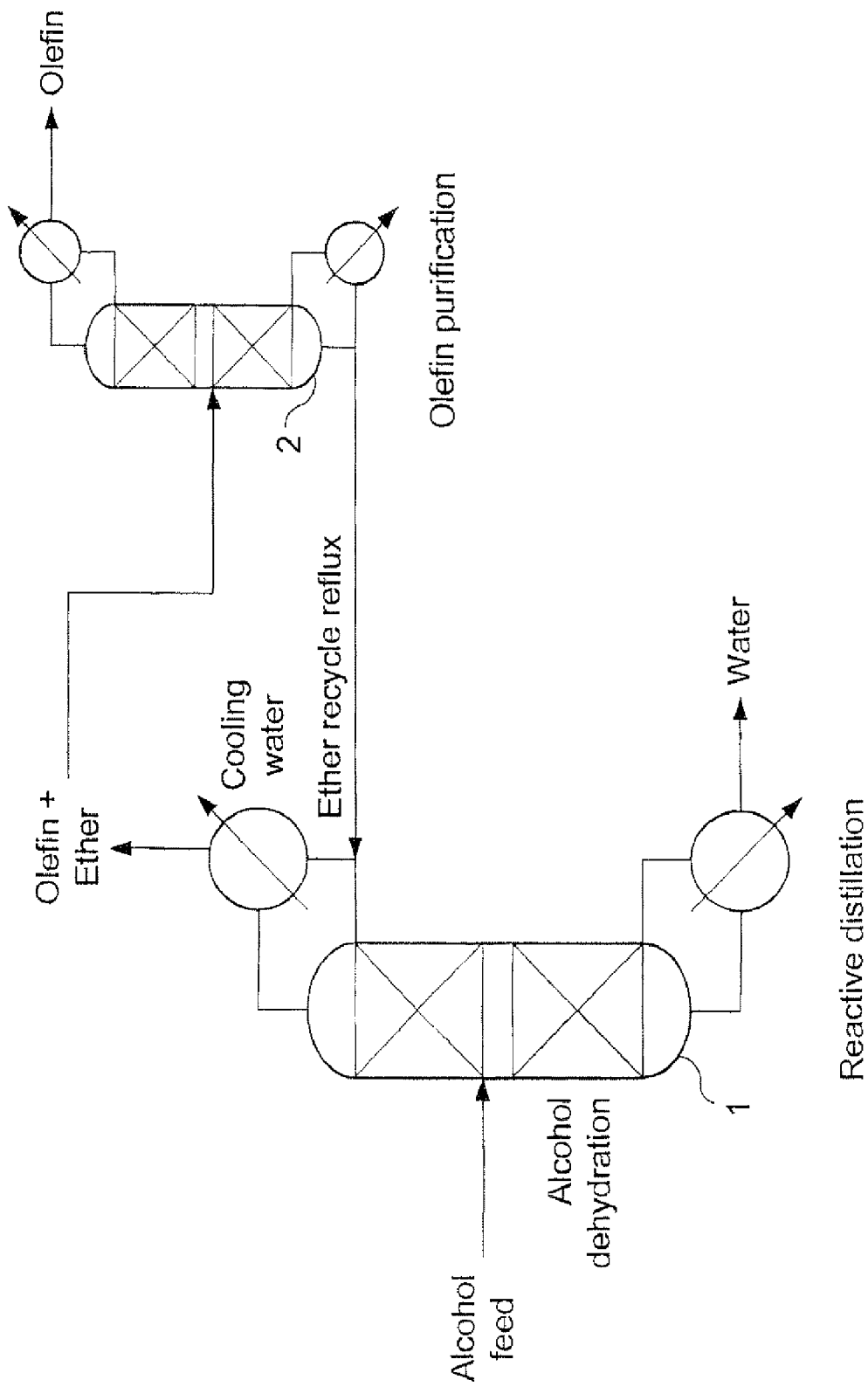

REACTIVE DISTILLATION FOR THE DEHYDRATION OF MIXED ALCOHOLS

This application is the U.S. national phase of International Application No. PCT/GB2006/002419 filed 29 Jun. 2006 which designated the U.S. and claims priority to European Patent Application No. 05254235.4 filed 6 Jul. 2005, the entire contents of each of which are hereby incorporated by reference.

The present invention relates to a process for the production of alkene(s) from a feedstock comprising of at least one monohydric aliphatic paraffinic alcohol.

BACKGROUND OF THE INVENTION

Olefin(s) have traditionally been produced by steam or catalytic cracking of hydrocarbons. However, inevitably as oil resources are decreasing, the price of oil is increasing; which makes light olefin(s) production a costly process. Thus there is an ever-growing need for non-petroleum routes to produce $C_2$+ olefin(s) essentially ethylene and propylene. Such olefin(s) are useful starting materials for numerous chemical products including polymeric products such as polyethylene.

In recent years the search for alternative materials for C2+ olefin(s) production has led to the use of alcohols such as methanol, ethanol and higher alcohols. The said alcohols may be produced by the fermentation of, for example, sugars and/or cellulosic materials.

Alternatively, alcohols may be produced from synthesis gas. Synthesis gas refers to a combination of hydrogen and carbon oxides produced in a synthesis gas plant from a carbon source such as natural gas, petroleum liquids, biomass and carbonaceous materials including coal, recycled plastics, municipal wastes, or any organic material. Thus, alcohol and alcohol derivatives may provide non-petroleum based routes for the production of olefin(s) and other related hydrocarbons.

Generally, the production of oxygenates, primarily methanol, takes place via three process steps. The three process steps are: synthesis gas preparation, methanol synthesis, and methanol purification. In the synthesis gas preparation step, an additional stage maybe employed by where the feedstock is treated, e.g. the feedstock is purified to remove sulfur and other potential catalyst poisons prior to being converted into synthesis gas. This treatment can also be conducted after syngas preparation; for example, when coal or biomass is employed.

Processes for producing mixtures of carbon oxide(s) and hydrogen (synthesis gas) are well known. Each has its advantages and disadvantages and the choice of using a particular reforming process is dictated by economic and available feed stream considerations, as well as by the desired mole ratio of H2:CO in the feedstock resulting from the reforming reaction. The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof. A discussion of these synthesis gas production technologies is provided in "Hydrocarbon Processing" V78, N.4, 87-90, 92-93 (April 1999) and "Petrole et Techniques", N. 415, 86-93 (July-August 1998). It is also envisaged that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438. Preferably, the synthesis gas is obtained via a "Compact Reformer" process as described in "Hydrocarbon Engineering", 2000, 5, (5), 67-69; "Hydrocarbon Processing", 79/9, 34 (September 2000); "Today's Refinery", 15/8, 9 (August 2000); WO 99/02254; and WO 200023689.

Typically, for commercial syngas production the pressure at which the synthesis gas is produced ranges from approximately 20 to 75 bar and the temperature at which the synthesis gas exits the reformer ranges from approximately 700 DEG C. to 1100 DEG C. The synthesis gas contains a molar ratio of hydrogen to carbon oxide—which is dependent on the syngas feedstock—ranging from 0.8 to 3.

The synthesis gas preparation, also known as reforming, may take place in a single-step wherein all of the energy consuming reforming reactions are accomplished in a single tubular steam reformer. The single-step reformer results in a production of surplus hydrogen. In a preferred alternative, the synthesis gas preparation may take place in a two-step reforming process wherein the primary reforming in a tubular steam reformer is combined with an oxygen-fired secondary reforming step which produces a synthesis gas with a deficiency in hydrogen. With this combination it is possible to adjust the synthesis gas composition to obtain the most suitable composition for methanol synthesis. As an alternative, autothermal reforming wherein a stand-alone, oxygen-fired reformer produces synthesis gas having a hydrogen deficiency followed by the downstream removal of carbon dioxide to restore the desired ratio of hydrogen to carbon oxide—results in a simplified process scheme with lower capital cost. The burner design is an important part of either oxygen-fired step. The burner mixes the hydrocarbon and oxygen and by combustion in the flame, heat is provided for conversion of the hydrocarbons The reaction from synthesis gas to oxygenates such as methanol is an exothermic equilibrium limited reaction which is favored by low temperatures. It also requires high pressures over a heterogeneous catalyst as the reactions which produce methanol exhibit a decrease in volume. As disclosed in U.S. Pat. No. 3,326,956, low-pressure methanol synthesis is based on a copper oxide-zinc oxide-alumina catalyst that typically operates at a nominal pressure of 5-10 MPa and temperatures ranging from approximately 150 DEG C. to 450 DEG C. over a variety of catalysts, including $CuO/ZnO/Al_2O_3$, $CuO/ZnO/Cr_2O_3$, $ZnO/Cr_2O_3$, Fe, Co, Ni, Ru, Os, Pt, and Pd. Catalysts based on ZnO for the production of methanol and dimethyl ether are preferred. The low-pressure, copper-based methanol synthesis catalyst is commercially available from suppliers such as BASF, ICI Ltd. of the United Kingdom, and Haldor-Topsoe. Methanol yields from copper-based catalysts are generally over 99.5% of the converted CO+CO2 present. Water is a by-product of the conversion of the synthesis gas to oxygenates. A paper entitled, "Selection of Technology for Large Methanol Plants," by Helge Holm-Larsen, presented at the 1994 World Methanol Conference, Nov. 30-Dec. 1, 1994, in Geneva, Switzerland, and herein incorporated by reference, reviews the developments in methanol production and shows how further reduction in costs of methanol production will result in the construction of very large plants with capacities approaching 10,000 metric tonnes per day.

U.S. Pat. No. 4,543,435 discloses a process for converting an oxygenate feedstock comprising methanol, dimethyl ether or the like in an oxygenate conversion reactor into liquid hydrocarbons comprising C2-C4 olefin(s) and C5@+hydrocarbons. The C2-C4 olefin(s) are compressed to recover an ethylene-rich gas. The ethylene-rich gas is recycled to the oxygenate conversion reactor.

U.S. Pat. No. 4,076,761 discloses a process for converting oxygenates to gasoline with the return of a hydrogen-rich gaseous product to a synthesis gas plant or the oxygenate conversion reaction zone.

U.S. Pat. No. 5,177,114 discloses a process for the conversion of natural gas to gasoline grade liquid hydrocarbons and/or olefin(s) by converting the natural gas to a synthesis gas, and converting the synthesis gas to crude methanol and/or dimethyl ether and further converting the crude methanol/dimethyl ether to gasoline and olefin(s). International Patent Application No. 93/13013 to Kvisle et al. relates to an improved method for producing a silicon-alumino-phosphate catalyst which is more stable to deactivation by coking. The patent discloses that after a period of time, all such catalysts used to convert methanol to olefin(s) (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air.

EPO publication No. 0 407 038A1 describes a method for producing dialkyl ethers comprising feeding a stream containing an alkyl alcohol to a distillation column reactor into a feed zone, contacting the stream with a fixed bed solid acidic catalytic distillation structure to form the corresponding dialkyl ether and water, and concurrently fractionating the ether product from the water and unreacted materials.

U.S. Pat. No. 5,817,906 describes a process for producing light olefin(s) from a crude oxygenate feedstock comprising alcohol and water. The process employs two reaction stages. Firstly, the alcohol is converted using reaction with distillation to an ether. The ether is then subsequently passed to an oxygenate conversion zone containing a metal aluminosilicate catalyst to produce a light olefin stream.

The methanol to olefin(s)—MTO— process can be described as the dehydrative coupling of methanol to olefin(s) and is a well known chemistry that can be employed to produce olefin(s) from alcohol(s). This mechanism is thought to proceed via a coupling of C1 fragments generated by the acid catalysed dehydration of methanol, possibly via a methyloxonium intermediate. However the main disadvantage of the said MTO process is that a range of olefin(s) are co-produced together with aromatic and alkane by-products, which in turn makes it very difficult and expensive to recover the desired olefin(s).

Molecular sieves such as the microporous crystalline zeolite and non-zeolitic catalysts, particularly silicoaluminophosphates (SAPO), are known to promote the conversion of oxygenates by methanol to olefin (MTO) chemistry to hydrocarbon mixtures. Numerous patents describe this process for various types of these catalysts: U.S. Pat. Nos. 3,928,483, 4,025,575, 4,252,479 (Chang et al.); U.S. Pat. No. 4,496,786 (Santilli et al.); U.S. Pat. No. 4,547,616 (Avidan et al.); U.S. Pat. No. 4,677,243 (Kaiser); U.S. Pat. No. 4,843,183 (Inui); U.S. Pat. No. 4,499,314 (Seddon et al.); U.S. Pat. No. 4,447,669 (Harmon et al.); U.S. Pat. No. 5,095,163 (Barger); U.S. Pat. No. 5,191,141 (Barger); U.S. Pat. No. 5,126,308 (Barger); U.S. Pat. No. 4,973,792 (Lewis); and U.S. Pat. No. 4,861,938 (Lewis).

However this reaction has a high activation energy step—possibly in the methanol or dimethylether production step—hence to achieve high conversion there is a need for high temperatures, e.g. 450° C., to drive the reactions forward. Conventionally various means such as a heated catalyst recycle, and downtherm heating systems have been implemented in such systems in order to obtain these high temperature conditions. Unfortunately operating at these said high temperatures leads to major problems, such as, catalyst deactivation, coking and by-product formation. In order to avoid these problems the reactions may be operated at lower temperatures, but this necessitates an expensive recycle of intermediates and reactants.

Another major disadvantage associated with this method is that the aromatic and alkane by-products are co-produced together with the olefin(s) and are both difficult and expensive to separate from the desired products e.g. separating ethylene and ethane is an expensive process.

These and other disadvantages of the prior art show that there is a need for an improved and/or alternative process for the production of C2+ alkene(s) from alcohols.

SUMMARY OF THE INVENTION

The present invention relates specifically to another method—other than the MTO process—to produce alkene(s) from alcohol(s). The said chemistry of the present invention is believed to proceed via the dehydration of C2+ alcohols to produce alkene(s).

The present invention relates to a process for the production of alkene(s) from a feedstock comprising at least one monohydric aliphatic paraffinic alcohols having from 2 to 5 carbon atoms characterised in the following steps;

1. the monohydric aliphatic paraffinic alcohol(s) containing 2 to 5 carbon atoms are converted in a reactive distillation column at elevated pressure and temperature into a heads stream comprising the corresponding same carbon number alkene(s) and ether(s),
2. the heads stream from step 1 is then separated into an ether(s) enriched stream and an alkene(s) enriched stream,
3. at least part, preferably all of the ether(s) enriched stream from step 2 is then recycled as a reflux return to the reactive distillation column,
4. simultaneously the alkene(s) enriched stream from step 2 is separated into alkene(s) and ether(s),
5. at least part, preferably all of the separated ether(s) from step 4 are then recycled into the said reactive distillation column, and then
6. an alkene(s) stream is recovered from step 4.

According to a preferred embodiment, the present invention provides a process for the conversion of hydrocarbon to alkene(s) comprising the steps of a. converting in a syngas reactor hydrocarbon into a mixture of carbon oxide(s) and hydrogen,
b. converting the said mixture of carbon oxide(s) and hydrogen from step a in the presence of a particulate catalyst in a reactor under a temperature comprised between 200 and 400° C. and a pressure of 50 to 200 bar into a feedstock comprising at least one monohydric aliphatic paraffinic alcohols having from 2 to 5 carbon atoms alcohols, and
c. proceeding according to hereabove steps 1 to 6 according to the present invention to produce the aforementioned alkenes.

According to the present invention the method for the production of alkene(s) from alcohol(s) proceeds via the dehydration of C2+ alcohols; for this to occur one or more alpha hydrogen(s) must be present e.g. phenol, neo-pentyl glycol, for example 2, 2,dimethyl-propan-1-ol will not dehydrate via this mechanism whereas ethanol, n-propanol and t-butanol will. These dehydration reactions are distinguished from the aforementioned MTO process in that although no coupling of carbon fragments is required in the dehydration process a C—C double bond is formed during the elimination of water and as a result very high selectivity can be achieved. In general the conditions employed in MTO process are much more severe than those employed in alcohol dehydration.

Advantageously, the process of the present invention i.e. the conversion of the feedstock to ether(s) and/or alkene(s) is conducted in a single reactive distillation column thereby reducing the capital and energy costs. The dehydration of the feedstock is believed to proceed by either the direct dehydration to alkene(s) and water;

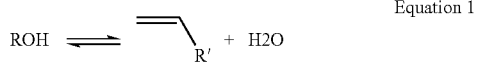

Equation 1 or via an ether intermediate;

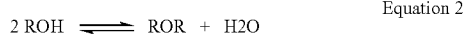

Equation 2

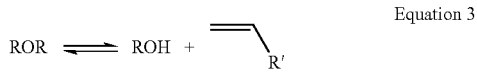

Equation 3 where R and R' are an ethyl, propyl, butyl or pentyl group.

All of the main reactions occurring in the reactive distillation column shown above are catalysed by acid catalysts. Equation 1, shows the endothermic direct elimination of alcohol to alkene(s) and water. Competing with Equation 1 are Equations 2 and 3; the exothermic etherification reaction (Equation 2), and the endothermic elimination of ether(s) to produce alkene(s) and alcohol (Equation 3). However, the overall dehydration of alcohols to alkene(s) is an endothermic process.

Equations 1, 2 and 3 are all equilibrium limited. However, according to the present invention, as all three reactions occur in the reactive distillation column, there is the added advantage in that there is an increased conversion for equilibrium limited reactions as a result of the continuous removal of products via distillation. This benefit is expected based on Le Châtelier's Principle, which states that if any disturbance is imposed on a system at equilibrium, the system will adjust itself to regain the equilibrium. Therefore, it is an added advantage of the present invention that the equilibrium limited reaction is increased beyond its thermodynamic limitation because of the continuous removal of the products via distillation and as a result there is an increased concentration of the reactants. Hence, the alkene product becomes concentrated at the top of the reactive distillation column together with the ether(s) and is termed the heads stream; and the water is concentrated in the base of the reactive distillation column as is known as the base product. The alcohol(s) and ether(s) having water azeotropes are of intermediate boiling point and are concentrated in the reaction zone of the reactive distillation column.

It is well known that when using a heterogeneous catalyst in the vapour phase, ethanol inhibits the elimination of diethyl ether (Reactions 2 and 3) by virtue of its stronger catalyst interaction. This can lead to a sequence of reactions. For example, when Ethanol is fed into a flow reactor with a dehydration catalyst, Equations 1 and 2 predominate until the ethanol concentration drops to a level were the ether can effectively compete for the catalytic sites. The competition of two reactants for an active site can be described by Langmuir Hinschelwood mechanism (e.g. Chemical Kinetics 3rd edition author K, J. Laidler P 249-251, Harper and Row publishers New York). An effect of this interaction for batch or flow reactors has been found to reduce the rate of ethylene production until the ethanol has been mostly consumed e.g. Collection of czechoslavak chemical comms 1986 51 (4) p763-73 V. Moravek and M. Kraus.

However, according to the present invention, another advantage is that through a combination of reaction and distillation this limitation can be overcome. For example in the reactive distillation column the ether(s) and alcohol(s) are separated accordingly by their azeotropes and by their boiling points. So ether(s) are concentrated onto the catalyst at different positions in the column from the alcohol(s) and hence this will result in the added advantage of decreased alcohol inhibition of the reaction.

The reactive distillation column in which the process is conducted refers to a combined distillation column and reactor. The internals of the reactive distillation column are arranged to provide a plurality of "theoretical plates" which assist the separation of the products from the reactants. The internals of the column are usually those used in conventional distillation for example, sieve plates, unstructured and structured packing, bubble cap and mixtures thereof. This particular apparatus is very effective at promoting vapor-liquid contacting and, therefore fractional distillation of the product(s) from the reactants. The catalyst(s) employed can be either homogeneous or heterogeneous, homogenous catalyst(s) being the preferred option.

According to the present invention when using heterogeneous catalyst(s), the catalyst(s) are positioned so that they have maximum interaction with reactants and reaction intermediates; this can be achieved by supporting the catalyst(s) on the column internals, for example ion exchange resins have been supported; in cloth bales, on sieve plates, fibreglass bags, in methyl tertiary butyl ether (MTBE) reactive distillation plants. The catalyst(s) can also provide the column packing, for example they can be coated, extruded, moulded into raschig rings or any other known type of column packing. The catalyst(s) can also be inter-dispersed with unmodified column packings. Heterogeneous catalyst(s) have an added advantage in that the separation of the reactants and products is trivial, that is, it is done by physical separation e.g. filtration.

According to the present invention suitable heterogeneous catalyst(s) include but are not limited to insoluble heteropolyacids, sulphonated supports (e.g. Nafion and ion exchange resins) zeolites, metal modified zeolites, mordenites and mixtures thereof; preferably heteropolyacids and ion-exchange resins; more preferably heteropolyacids; and most preferably salts of 12-tungstosilicic acid and 18-tungstophosphoric acid.

The heteropolyacids of the present invention are complex, high molecular weight anions comprising oxygen-linked polyvalent metal atoms. Typically, each anion comprises 12-18, oxygen-linked polyvalent metal atoms. The polyvalent metal atoms, known as peripheral atoms, surround one or more central atoms in a symmetrical manner. The peripheral atoms may be one or more of molybdenum, tungsten, vanadium, niobium, tantalum, or any other polyvalent metal. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable heteropolyacids include Keggin, Wells-Dawson and Anderson-Evans-Perloff heteropolyacids. Specific examples of suitable heteropolyacids are as follows:

| 18-tungstophosphoric acid | $H_6[P_2W18O62] \cdot xH2O$ |
|---|---|
| 12-tungstophosphoric acid | $H3[PW12O40] \cdot xH2O$ |
| 12-molybdophosphoric acid | $H3[PMo12O40] \cdot xH2O$ |
| 12-tungstosilicic acid | $H4[SiW12O40] \cdot xH2O$ |
| 12-molybdosilicic acid | $H4[SiMo12O40] \cdot xH2O$ |
| Cesium hydrogen tungstosilicate | $Cs3H[SiW12O40] \cdot xH2O$ | and the free acid or partial salts of the following heteropolyacids:

| Potassium tungstophosphate | $K6[P2W18O62] \cdot xH2O$ |
|---|---|
| Sodium molybdophosphate | $Na3[PMo12O40] \cdot xH2O$ |
| Ammonium molybdodiphosphate | $(NH4)6[P2Mo18O62] \cdot xH2O$ |
| Potassium molybdodivanado phosphate | $K5[PMoV2O40] \cdot xH2O$ |

The heteropolyacids employed in the present invention may have molecular weights of more than 700 and less than 8500, preferably more than 2800 and less than 6000. Such heteropolyacids also include dimeric complexes.

To prepare the catalysts that can advantageously be used in the present invention, a catalyst support is impregnated with a non-aqueous solution of the heteropolyacid and the catalyst is precipitated by preparing a low solubility salt in situ. Such a solution is prepared by dissolving the heteropolyacid in a non-aqueous solvent. Suitable solvents include polar solvents such alcohols, ketones and aldehydes. Suitable alcohols include C1 to $C_8$ alcohols, preferably, $C_1$ to $C_4$ alcohols and most preferably methanol and ethanol. Suitable ketones are $C_2$ to $C_4$ ketones e.g. acetone. The concentration of heteropolyacid in the solution is preferably 10 to 80 wt %, more preferably 20 to 60 wt % and most preferably 30 to 50 wt %.

The impregnation may be carried out using the incipient wetness technique, with a partial neutralization stage to prepare the insoluble catalyst. Any suitable drying technique may be employed, with evaporation in a standard rotary evaporator being preferred.

Alternatively, the catalyst support may be immersed in the aqueous solution, and left to soak and then a solution of counterion added to precipitate the HPA onto the support. The impregnated support may then be washed and dried. This may be achieved using any conventional separation technique, including, for example, decantation and/or filtration. Once recovered, the impregnated support may be dried, preferably by placing the support in an oven. Alternatively, or additionally, a desiccator may be employed. The amount of heteropolyacid impregnated on the support is suitably in the range of 10 wt % to 60 wt % and preferably 30 wt % to 50 wt % based on the total weight of the heteropolyacid and the support.

Suitable catalyst supports include silica supports, such as silica gel supports and supports produced by the flame hydrolysis of SiCl4. Preferred supports are substantially free of extraneous metals or elements which might adversely affect the catalytic activity of the system. Thus, suitable silica supports are at least 99% w/w pure. Impurities amount to less than 1% w/w, preferably less than 0.60% w/w and more preferably less than 0.30% w/w. The pore volume of the support is 0.3-1.2 ml/g, preferably 0.6-1.0 ml/g. The average pore radius (prior to use) of the support is 10 to 500 Å, preferably 30 to 100 Å. The support has a crush strength of at least 2 Kg force, suitably at least 5 Kg force, preferably at least 6 Kg and more preferably at least 7 Kg. The bulk density of the support is at least 380 g/l, preferably at least 440 g/l.

Suitable silica gel supports include Grace 57 and 1371, Grace No. 1371 being preferred. Grace No. 1371 has an average particle size of 0.1-3.5 mm. However, these particles may be crushed and sieved to smaller sizes of, for example, 0.5-2 mm, if desired.

Suitable supports produced by the flame hydrolysis of $SiCl_4$ may be prepared by the pelletisation of AEROSIL® 200 (ex Degussa). An example of such a support is Support 350. Suitable pelletisation procedures are described in U.S. Pat. No. 5,086,031, particularly in the examples. The average particle diameter of the pellets is 2 to 10 mm, preferably 4 to 6 mm.

A further embodiment of the said invention is where the catalyst support, as used in the present invention, is first treated with a fluorinating agent; it is believed that due to the highly electronegative nature of fluorine the resulting effect is that the electronic properties of catalyst support will be modified and it is believed that this allows the following advantages: inertness of support and/or improved acidity, thus improving the overall selectivity and/or activity of the catalyst.

Fluorinating agents that can be used to treat the support may comprise, but are not limited to; hydrogen fluoride, aqueous solutions of hydrofluoric acid, mixtures of hydrofluoric acid with lesser amounts of other acids such as hydrochloric or acetic acids or acid solutions to which certain aluminum salts have been added or weak solutions of hydrofluosilicic acid containing an aluminum salt. The treatment of the said catalyst support with aqueous hydrofluoric acid solutions may be performed by soaking the catalyst particles in a solution of the acid of between 1 to 8% acid for a period of between 1 to 24 hours. The fluorinated support can then be impregnated with the catalyst of choice.

According to the present invention homogeneous catalyst (s) can also be employed in the reactive distillation column. The preferred homogeneous catalyst(s) are of a higher boiling point than the reactants and products and as result will reside predominately in the column liquid phase(s) and eventually concentrate in the reaction kettle. The interaction between these said catalyst(s) and reactants in the reaction zone can be controlled by varying the amount of catalyst(s) recycled into the reactive distillation column and by changing the columns' internals to increase the liquid hold up. The separation of the homogeneous catalysts from the water accumulating in the reboiler can be achieved by condensing above the reboiler a vapour stream of predominately pure water. Added advantages of using a homogeneous catalyst(s) are that the concentration of catalyst can be altered freely and that the deactivated catalysts can easily be eliminated from the system and replaced by fresh catalyst. The recovered homogeneous catalyst solution from the reboiler is then recycled to the column. One or more addition points maybe employed to concentrate the catalyst where required.

Suitable homogeneous catalysts include but are not limited to sulphonic acids such as methane sulphonic acid, para-toluene sulphonic acid, triflic acid, sulphuric acids, heteropolyacids and phosphoric acid; phosphoric acid and organosulphonic acids are preferred. According to the present invention the alkene(s) and ether(s) heads stream that is extracted from the top of the reactive distillation column contains a mixture of both ether(s) and alkene(s). At least part—preferably at least 80 wt %; more preferably at least 90 wt %; most preferably at least 97 wt %; even more preferably at least 99 wt %—of the ether(s) are then separated from the alkene(s). At least part—preferably all—of the ether(s) separated are then recycled back into the top of the reactive distillation column as a reflux.

According to the present invention this separation is performed in at least two consecutive steps. Firstly, the heads stream from step 1 is separated into an ether(s) enriched stream and an alkene(s) enriched stream. Preferably, the ether(s) enriched stream comprises at least 80 wt % of the ether(s) from the heads stream. Then, at least part, preferably all of the ether(s) enriched stream from step 2 is recycled as a reflux return into the reactive distillation column.

Secondly, the alkene(s) enriched stream from step 2 is separated into ether(s) and alkene(s). Then at least part, preferably all of the separated ether(s) are recycled back into the reactive distillation column, and an alkene(s) stream is recovered. The recycling of the recovered ether(s) (step 5), can be done either as a reflux return directly into the reactive distillation column or as a co-feed with the heads stream in step 2.

The ether(s) that are recovered and recycled are essentially C2-C5 alcohol derived ether(s) such as diethyl ether, n-propyl ether, iso-propyl ether and the butyl ether(s) and the recovered alkene(s) from the reactive distillation column are essentially ethylene and n-propylene.

The thermodynamic studies have shown that the present invention allows the dehydration of a mixture of ethanol and n-propanol into corresponding alkene(s) to be conducted with a much higher selectivity and an unexpected high conversion. This said higher conversion improves the economics of the process dramatically as due to a lack of by-products there is no longer a need to perform expensive separations of by-products and products which is currently required with the MTO process.

The outlet from the bottom of the reactive distillation column eliminates predominately excess water in order to maintain a balanced medium within the column.

The crude oxygenate feedstock that is introduced into the reactive distillation column comprises of at least one $C_2$-$C_5$ alcohol which may be, for example, ethanol, n-propanol, iso-propanol, n-butanol, iso-butanol, n-pentanol, iso-pentanol and mixtures thereof. Typically, a mixture of at least two alcohols will be employed which will be selected from monohydric aliphatic paraffinic alcohols having from 2 to 5 carbon atoms, preferably a mixture of at least two alcohols selected from monohydric aliphatic paraffinic alcohols having from 2 to 4 carbon atoms will be used, more preferably a mixture of at least two alcohols selected from monohydric aliphatic paraffinic alcohols having from 2 to 3 carbon atoms will be used and most preferably a mixture of ethanol and n-propanol will be used. Preferably, the alcohol introduced into the reactive distillation column, consists of ethanol, n-propanol, and/or the mixtures thereof. More preferably, the alcohol introduced into the reactive distillation column, consists of ethanol.

According to the present invention water is permissible in the crude oxygenate feedstock; in the preferred mode of operation the crude oxygenate feedstock may comprise up to 50 wt % of water. In another mode, that utilises the ability of a reactive distillation column to effectively separate water, crude bioethanol and other bioalcohol(s) which can comprise mostly of water may be used.

According to the most preferred embodiment of the present invention the C2-C5 alcohols together with the water represent at least 90 wt % of the crude oxygenate feedstock introduced into the reactive distillation column.

In another embodiment, the reactive distillation can have as a co-feed a stream of ethers as previously defined.

According to another embodiment of the present invention the pressure at which the reactive distillation column operates is more than 1.5 MPa but less than 4.0 MPa and preferably more than 1.8 MPa but less than 2.7 MPa. The temperature employed in the column is controlled by the boiling point of the specified components at the given pressure, it is preferably in the range of 150° C. to 250° C. Temperatures and pressures outside of the stated limits are not excluded, however they do not fall under the preferred embodiments of the present invention.

BRIEF DESCRIPTION OF THE DRAWINGS

FIG. 1 represents one embodiment of a process scheme according to the present invention. This said embodiment comprises optional and/or preferred process steps according to the present invention.

EXAMPLE

The following example is based on an engineering simulation using Aspen software supplied by Aspen Technology Inc.:

Example The feed, consisting of 500 kte/y (57 te/h) of 80% ethanol, 20% water is fed into a reactive distillation column (column 1). The column consists of 40 theoretical trays (plates). The feed enters the said column on tray 30, and the reactive section was set from trays 10 to 20 (numbered from the top). The reaction is assumed to be fast, that is, equilibrium is achieved on each tray. The top of the reactive distillation column is also equipped with a partial condenser (using cooling water at 40° C.). The reboiler is positioned at the base of the said column and is operated with steam.

The overhead vapour from the partial condenser of the reactive distillation column flows to base of column 2, where column 2 consists of 20 theoretical trays. Vapour flow from the overhead of column 2 is partially condensed by refrigeration, at −40° C. The liquid from the base of column 2 is returned to the reactive distillation column, as a reflux return.

The vapour take-off from the top of the reactive distillation column after partial condensation was found to consist of ethylene with approximately 5.67% w/w diethyl ether (DEE), 0.14% w/w water and less than 1 ppm ethanol.

The vapour take-off from the top of column 2 was found to contain ethylene with approximately 1 ppm DEE, negligible water and ethanol.

The liquid product from the base of the reactive distillation column, was found to contain water, with a negligible level of impurity, suitable for discharge direct to effluent.

For completeness, the model also gave the following heat exchange duties:

Reactive distillation condenser: 29.5 MW

Column 2 condenser: 3.0 MW

Reactive distillation reboiler: 37.3 MW

This illustrates the advantage of employing partial condensation on the reactive distillation together with an ethylene polishing column 2. The expensive refrigerated condenser duty required for olefin polishing has been reduced considerably by separating it from the reactive distillation column.

| | Mass Balance | | | | |
|---|---|---|---|---|---|
| | Feed Kmol/h | Vapour Col 1->2 Kmol/h | Liquid Col 2->1 Kmol/h | Overhead Product (column 2) Kmol/h | Base Product (column 1) Kmol/h |
| DEE | 0.0 | 62.5 | 62.5 | 0.0 | 0.0 |
| Ethanol | 991.2 | 0.0 | 0.0 | 0.0 | 0.0 |
| Ethylene | 0.0 | 1037.4 | 46.2 | 991.2 | 0.0 |
| Water | 633.7 | 1.5 | 1.5 | 0.0 | 1624.9 |

The invention claimed is:

1. Process for the production of alkene(s) from a feedstock comprising at least one monohydric aliphatic paraffinic alcohol having from 2 to 5 carbon atoms, comprising the following steps:
   1. converting the monohydric aliphatic paraffinic alcohol(s) containing 2 to 3 carbon atoms in a reactive distillation column at elevated pressure and temperature into a heads stream comprising the corresponding same carbon number alkene(s) and ether(s),
   2. separating the heads stream from step 1 into an ether(s) enriched stream and an alkene(s) enriched stream,
   3. recycling at least part of the ether(s) enriched stream from step 2 as a reflux return to the reactive distillation column,
   4. simultaneously separating the alkene(s) enriched stream from step 2 onto alkene(s) and ether(s),
   5. recycling at least part of the separated ether(s) from step 4 into said reactive distillation column, and then
   6. recovering an alkene(s) stream from step 4.

2. Process for the conversion of hydrocarbon to alkene(s) comprising the steps of:
   a. converting in a syngas reactor hydrocarbon into a mixture of carbon oxide(s) and hydrogen,
   b. converting said mixture of carbon oxide(s) and hydrogen from step a in the presence of a particulate catalyst in a reactor under a temperature comprised between 200 and 400° C. and a pressure of 50 to 200 bar into a feedstock comprising at least one monohydric aliphatic paraffinic alcohol having from 2 to 3 carbon atoms alcohols, and
   c. proceeding according to steps 1 to 6 according to claim 1 to produce said alkene(s).

3. Process according to claim 1 wherein the reactive distillation column employs a heterogeneous catalyst selected from the group consisting of insoluble heteropolyacids, sulphonated supports, zeolites, metal modified zeolites, mordenites and mixtures thereof.

4. Process according to claim 3 wherein the heterogeneous catalyst is supported on a support which is first treated with a fluorinating agent.

5. Process according to claim 1 wherein the reactive distillation column employs a homogeneous catalyst.

6. Process according to claim 5 wherein the homogeneous catalyst is a sulphonic acid.

7. Process according to claim 1 wherein at least part of the ether(s) are then separated from the alkene(s) coming from the alkene(s) and ether(s) heads stream that is extracted from the top of the reactive distillation column.

8. Process according to claim 7 wherein at least part of the ether(s) separated are then recycled back into the top of the reactive distillation column as a reflux.

9. Process according to claim 1 wherein the ether(s) that are recovered and recycled are essentially $C_2$-$C_3$ alcohol derived ether(s) and the recovered alkene(s) from the reactive distillation column are essentially ethylene and n-propylene.

10. Process according to claim 1 wherein the feedstock that is introduced into the reactive distillation column comprises at least one $C_2$-$C_3$ alcohol.

11. Process according to claim 1 wherein the feedstock comprises water, and the $C_2$-$C_3$ alcohols together with the water represent at least 90 wt % of the crude oxygenate feedstock introduced into the reactive distillation column.

12. Process according to claim 1 wherein an additional ether feed is added to the alcohol(s) fed to the reactive distillation column.

13. Process according to claim 1 wherein in step 3 all of the ether(s) enriched stream from step 2 is recycled as a reflux return to the reactive distillation column.

14. Process according to claim 1 wherein in step 5 all of the separated ether(s) from step 4 are recycled into said reactive distillation column.

15. Process according to claim 3 wherein the sulphonated supports are selected from the group consisting of Nafion and ion exchange resins.

16. Process according to claim 3 wherein the heterogeneous catalyst is selected from the group consisting of heteropolyacids and ion-exchange resins.

17. Process according to claim 16 wherein the heterogeneous catalyst is a heteropolyacid.

18. Process according to claim 3 wherein the heterogeneous catalyst is selected from the group consisting of salts of 12-tungstosilicic acid and 18-tungstophosphoric acid.

19. Process according to claim 5 wherein the homogeneous catalyst used in the reactive distillation reactor has a higher boiling point than the reactants and products.

20. Process according to claim 6 wherein the sulphonic acid catalyst is selected from the group consisting of methane sulphonic acid, para-toluene sulphonic acid, triflic acid, sulphuric acids, heteropolyacids and phosphoric acid; phosphoric acid and organosulphonic acids.

21. Process according to claim 7 wherein at least 80 wt % of the ether(s) are separated from the alkene(s) coming from the alkene(s) and ether(s) heads stream that is extracted from the top of the reactive distillation column.

22. Process according to claim 7 wherein at least 90 wt % of the ether(s) are then separated from the alkene(s) coming from the alkene(s) and ether(s) heads stream that is extracted from the top of the reactive distillation column.

23. Process according to claim 7 wherein at least 97 wt % of the ether(s) are then separated from the alkene(s) coming from the alkene(s) and ether(s) heads stream that is extracted from the top of the reactive distillation column.

24. Process according to claim 1 wherein at least 99 wt % of the ether(s) are then separated from the alkene(s) coming from the alkene(s) and ether(s) heads stream that is extracted from the top of the reactive distillation column.

25. Process according to claim 8 wherein all of the ether(s) separated are then recycled back into the top of the reactive distillation column as a reflux.

26. Process according to claim 9 wherein the ether(s) that are recovered and recycled are diethyl ether, n-propyl ether and iso-propyl ether.

27. Process according to claim 10 wherein the $C_2$-$C_3$ alcohol is selected from the group consisting of ethanol, n-propanol, iso-propanol and mixtures thereof.

28. Process according to claim 27 wherein the mixtures thereof comprise a mixture of ethanol and n-propanol.

* * * * *